(12) United States Patent
Wang et al.

(10) Patent No.: US 12,290,386 B1
(45) Date of Patent: May 6, 2025

(54) MULTI-LEAD ELECTROCARDIOGRAM (ECG) SIGNAL CLASSIFICATION METHOD BASED ON SELF-SUPERVISED LEARNING

(71) Applicants: Qilu University of Technology (Shandong Academy of Sciences), Jinan (CN); SHANDONG COMPUTER SCIENCE CENTER (NATIONAL SUPERCOMPUTING CENTER IN JINAN), Jinan (CN)

(72) Inventors: Yinglong Wang, Jinan (CN); Wei Liu, Jinan (CN); Minglei Shu, Jinan (CN); Pengyao Xu, Jinan (CN); Shuwang Zhou, Jinan (CN); Zhaoyang Liu, Jinan (CN)

(73) Assignees: QILU UNIVERSITY OF TECHNOLOGY (SHANDONG ACADEMY OF SCIENCES), Jinan (CN); SHANDONG COMPUTER SCIENCE CENTER (NATIONAL SUPERCOMPUTING CENTER IN JINAN), Jinan (CN)

( * ) Notice: Subject to any disclaimer, the term of this patent is extended or adjusted under 35 U.S.C. 154(b) by 0 days.

(21) Appl. No.: 18/664,341

(22) Filed: May 15, 2024

(30) Foreign Application Priority Data

Nov. 8, 2023 (CN) .......................... 202311479336.6

(51) Int. Cl.
*A61B 5/00* (2006.01)
*G06N 3/0895* (2023.01)
*G16H 50/20* (2018.01)

(52) U.S. Cl.
CPC ......... *A61B 5/7267* (2013.01); *G06N 3/0895* (2023.01); *G16H 50/20* (2018.01)

(58) Field of Classification Search
CPC ..... A61B 5/7267; G16H 50/20; G06N 3/0895
See application file for complete search history.

(56) References Cited

U.S. PATENT DOCUMENTS

| 11,568,991 B1 | 1/2023 | Jain et al. |
| 2021/0026453 A1 | 1/2021 | Ketyko et al. |

(Continued)

FOREIGN PATENT DOCUMENTS

| CN | 113598784 A | 11/2021 |
| CN | 113679393 A | 11/2021 |

(Continued)

OTHER PUBLICATIONS

Prateek Singh, "Attention-Based Convolutional Denoising Autoencoder for Two-Lead ECG Denoising and Arrhythmia Classification, " IEEE Transactions On Instrumentation and Measurement, vol. 71, 2022; Digital Object Identifier 10.1109/TIM.2022.3197757. (Year: 2022).*

(Continued)

*Primary Examiner* — Jonathon A. Szumny
(74) *Attorney, Agent, or Firm* — Bayramoglu Law Offices LLC (57) ABSTRACT

A multi-lead electrocardiogram (ECG) signal classification method based on self-supervised learning relates to the technical field of ECG signal classification. The method includes: processing an original signal through different data augmentation methods, designing an appropriate encoder module, extracting a feature of an ECG signal through a large amount of easily available unlabeled data such that an encoder learns more class information of the ECG signal, fine-tuning the model encoder with a small amount of labeled data for feature optimization, and continuously optimizing a parameter of a feature extractor by training a model such that a generated feature well reflects a structure and information of input data. Through self-supervised learning, (Continued)

the method reduces obstacles caused by performing ECG signal classification through a large amount of expensive manually labeled data, improving the generalization ability of the model.

9 Claims, 6 Drawing Sheets

(56) References Cited

U.S. PATENT DOCUMENTS

| | | | |
|---|---|---|---|
| 2021/0304855 A1* | 9/2021 | Ansari | G16H 50/20 |
| 2021/0374570 A1 | 12/2021 | Cheng et al. | |
| 2022/0084679 A1* | 3/2022 | Lee | G06N 3/088 |
| 2023/0306267 A1* | 9/2023 | Jacob Banville | G06N 3/0464 |

FOREIGN PATENT DOCUMENTS

| | | |
|---|---|---|
| CN | 114190952 A | 3/2022 |
| CN | 114881105 A | 8/2022 |
| CN | 115568860 A | 1/2023 |
| CN | 115607164 A | 1/2023 |
| CN | 115813408 A | 3/2023 |
| CN | 115836849 A | 3/2023 |
| CN | 115881308 A | 3/2023 |
| CN | 116843013 A | 10/2023 |
| KR | 102461646 B1 | 11/2022 |
| WO | 2020061987 A1 | 4/2020 |
| WO | WO-2023114742 A1 * | 6/2023 ............. A61B 5/257 |
| WO | WO-2023229861 A1 * | 11/2023 ............. G06V 30/10 |

OTHER PUBLICATIONS

Xu et al. "Interpretation of Electrocardiogram (ECG) Rhythm by Combined CNN and BILSTM," IEEE Access; Digital Object Identifier 10.1109/ACCESS.2020.3006707. (Year: 2020).*

Gramfort et al., "Learning with self-supervision on EEG data," 2021 9th International Winter Conference on Brain-Computer Interface (BCI) | 978-1-7281-8485-2/21/ © 2021 IEEE | DOI: 10.1109/BCI51272.2021.9385345. (Year: 2021).*

Yehuda et al., "Self-supervised Classification of Clinical Multivariate Time Series using Time Series Dynamics," KDD '23, Aug. 6-10, 2023, Long Beach, CA, USA; https://doi.org/10.1145/3580305.3599954. (Year: 2023).*

Mehari et al., "Self-supervised representation learning from 12-lead ECG data," Computers in Biology and Medicine 141 (2022) 105114; https://doi.org/10.1016/j.compbiomed.2021.105114. (Year: 2022).*

Wang et al., "Self-Supervised EEG Emotion Recognition Models Based on CNN," IEEE Transactions On Neural Systems and Rehabilitation Engineering, vol. 31, 2023; Digital Object Identifier 10.1109/TNSRE.2023.3263570. (Year: 2023).*

* cited by examiner

MULTI-LEAD ELECTROCARDIOGRAM (ECG) SIGNAL CLASSIFICATION METHOD BASED ON SELF-SUPERVISED LEARNING

CROSS REFERENCE TO THE RELATED APPLICATIONS

This application is based upon and claims priority to Chinese Patent Application No. 202311479336.6, filed on Nov. 8, 2023, the entire contents of which are incorporated herein by reference.

TECHNICAL FIELD

The present disclosure relates to the technical field of electrocardiogram (ECG) signal classification, and in particular, to a multi-lead ECG signal classification method based on self-supervised learning.

BACKGROUND

Electrocardiogram (ECG) signals are important electrical signals used to record heart activity information. Different ECG signals have different meanings, so it is crucial to correctly classify them. With the development of artificial intelligence (AI), feature extraction and classification of ECG signals can be implemented through neural networks. However, these network architectures are usually based on supervised learning tasks and rely on a large amount of labeled data, ignoring unlabeled data that also contributes to ECG signal classification. In addition, when applied to different datasets, traditional neural networks often suffer from the influence of dataset differences, thereby weakening the generalization ability of the model and making the model hard to leverage its advantages.

SUMMARY

In order to overcome the above technical shortcomings, the present disclosure provides a multi-lead ECG signal classification method based on self-supervised learning, which improves the accuracy and generalization ability of a classification model.

In order to solve the technical problem, the present disclosure adopts the following technical solution.

A multi-lead ECG signal classification method based on self-supervised learning includes the following steps:
a) acquiring original ECG signal data X;
b) preprocessing the original ECG signal data X to acquire a preprocessed ECG signal X';
c) constructing a data augmentation unit, inputting the preprocessed ECG signal X' into the data augmentation module, and outputting an augmented positive sample $X_a$ and an augmented negative sample $Y_a$;
d) constructing an encoder module; inputting the augmented positive sample $X_a$ into the encoder module, and outputting an encoded sequence $X_c$; and inputting the augmented negative sample $Y_a$ into the encoder module, and outputting an encoded sequence $Y_c$;
e) constructing a feature dimensionality reconstruction module; inputting the encoded sequence $X_c$ into the feature dimensionality reconstruction module, and outputting a dimensionality-reconstructed lead feature $X_g$; and inputting the encoded sequence $Y_c$ into the feature dimensionality reconstruction module, and outputting a dimensionality-reconstructed lead feature $Y_g$;
f) training, by an adaptive moment estimation (Adam) optimizer, the encoder module through a contrastive learning loss to acquire a trained encoder module;
g) replacing the original ECG signal data X in the step b) with ECG signal data Z that needs classification, and repeating the step b) to acquire a preprocessed ECG signal Z';
h) inputting the preprocessed ECG signal Z' into the trained encoder module, and outputting an encoded sequence $Z_c$;
i) replacing the encoded sequence $X_c$ in the step e) with the encoded sequence $Z_c$, and repeating the step e) to acquire a dimensionality-reconstructed lead feature $Z_g$; and
j) acquiring a final class based on the lead feature $Z_g$.

Further, the step a) includes: acquiring an ECG signal from a PhysioNet2020 dataset, resampling the acquired ECG signal by a resample( ) function in a Python library sklearn.utils, and adjusting a length of the ECG signal to L sample points to acquire the original ECG signal data X, $X \in R^{C \times L}$, where R denotes a real number space, and C denotes a number of channels.

Preferably, C=12, and L=1000.

Further, the step b) includes:
b-1) calling, by python, a signal.butter method from a scipy module; and
performing, by a Butterworth bandpass filter with a cutoff frequency including a low frequency of 0.5 Hz and a high frequency of 49 Hz, denoising and baseline wander removal on the original ECG signal data X; and
b-2) resampling, by the resample( ) function in the Python library sklearn.utils, an acquired ECG signal for each lead in the original ECG signal data X after denoising and baseline wander removal; and adjusting a length of the ECG signal to L to acquire the preprocessed ECG signal X'.

Further, the step c) includes:
c-1) constructing the data augmentation unit, including a first augmentation module and a second augmentation module;
c-2) inputting the preprocessed ECG signal X' into the first augmentation module, and multiplying a value of each lead signal in the preprocessed ECG signal X' by −1 to acquire the augmented positive sample X; and
c-3) inputting the preprocessed ECG signal X' into the second augmentation module, and performing data augmentation on the preprocessed ECG signal X' through Gaussian noise to acquire the augmented negative sample $Y_a$.

Further, the step d) includes:
d-1) constructing the encoder module, including a one-dimensional convolutional layer, a time-domain fusion module temporal convolutional fusion network (TCFN), an average pooling layer, and a Dropout layer;
d-2) inputting the augmented positive sample $X_a$ into the one-dimensional convolutional layer, and outputting a feature $X_{c1}$; and inputting the augmented negative sample Y into the one-dimensional convolutional layer, and outputting a feature Y;
d-3) dividing the time-domain fusion module TCFN into a first branch, a second branch, and a third branch;
d-4) constructing the first branch, including a first convolutional block, a second convolutional block, a third convolutional block, and a fourth convolutional block, where each of the first convolutional block, the second convolutional block, the third convolutional block, and the fourth convolutional block includes a first convolutional layer, a second convolutional layer, a BatchNormal1d layer, a rectified linear unit (ReLU) layer, a MaxPool1d layer, and a Dropout layer in sequence; inputting the feature $X_{c1}$ into the first convolutional block in the first branch, and outputting a feature $X_{c1}^1$; inputting the feature $X_{c1}^1$ into the second convolutional block in the first branch, and outputting a feature $X_{c1}^2$; inputting the feature $X_{c1}^2$ into the third convolutional block in the first branch, and outputting a feature $X_{c1}^3$; inputting the feature $X_{c1}^3$ into the fourth convolutional block in the first branch, and outputting a feature $X_{c1}'$; inputting the feature $Y_{c1}$ into the first convolutional block in the first branch, and outputting a feature $Y_{c1}^1$; inputting the feature $Y_{c1}^1$ into the second convolutional block in the first branch, and outputting a feature $Y_{c1}^2$; inputting the feature $Y_{c1}^2$ into the third convolutional block in the first branch, and outputting a feature $Y_{c1}^3$; and inputting the feature $Y_{c1}^3$ into the fourth convolutional block in the first branch, and outputting a feature $Y_{c1}'$;

d-5) constructing the second branch, including a lead memory module LM_Block and a skip connection module, where the lead memory module LM_Block includes a global pooling layer, a long short-term memory (LSTM) layer, a one-dimensional convolutional layer, and a Relu activation function in sequence; inputting the feature $X_{c1}$ into the lead memory module LM_Block, and outputting a feature $X_{c11}$; inputting the feature $X_{c11}$ and the feature $X_{c1}$ into the skip connection module for an addition operation to acquire a feature $X_{c1}''$; inputting the feature $Y_{c1}$ into the lead memory module LM_Block, and outputting a feature $Y_{c11}$; and inputting the feature $Y_{c11}$ and the feature $Y_{c1}$ into the skip connection module for an addition operation to acquire a feature $Y_{c1}''$;

d-6) constructing the third branch, including an attention module, a first one-dimensional convolutional layer, a second one-dimensional convolutional layer, a third one-dimensional convolutional layer, and a maximum pooling layer; inputting the feature $X_{c1}$ into the attention module, and performing, by a torch.nn.MultiheadAttention function in python, an attention operation on the feature $X_{c1}$ to obtain a resulting feature; inputting the resulting feature into the first one-dimensional convolutional layer, the second one-dimensional convolutional layer, the third one-dimensional convolutional layer, and the maximum pooling layer in sequence, and outputting an encoded sequence $X_{c1}'''$; inputting the feature $Y_{c1}$ into the attention module, and performing, by the torch.nn.MultiheadAttention function in python, an attention operation on the feature $Y_{c1}$ to obtain a resulting feature; and inputting the resulting feature into the first one-dimensional convolutional layer, the second one-dimensional convolutional layer, the third one-dimensional convolutional layer, and the maximum pooling layer in sequence, and outputting an encoded sequence $Y_{c1}'''$; and d-7) subjecting the feature $X_{c1}'$, the feature $X_{c1}''$, and the encoded sequence $X_{c1}'''$ to addition and averaging to acquire a feature $X_{c2}$; subjecting the feature $Y_{c1}'$, the feature $Y_{c1}''$, and the encoded sequence $Y_{c1}'''$ to addition and averaging to acquire a feature $Y_{c2}$; inputting the feature $X_{c2}$ into the average pooling layer and the Dropout layer of the encoder module in sequence, and outputting the encoded sequence $X_c$; and inputting the feature $Y_{c2}$ into the average pooling layer and the Dropout layer of the encoder module in sequence, and outputting the encoded sequence $Y_c$.

Preferably, in the step d-1), the one-dimensional convolutional layer of the encoder module includes a convolutional kernel with a size of 3; in the step d-4), each of the first convolutional layer and the second convolutional layer in the first convolutional block includes a convolutional kernel with a size of 64, each of the first convolutional layer and the second convolutional layer in the second convolutional block includes a convolutional kernel with a size of 32, each of the first convolutional layer and the second convolutional layer in the third convolutional block includes a convolutional kernel with a size of 16, and each of the first convolutional layer and the second convolutional layer in the fourth convolutional block includes a convolutional kernel with a size of 3; in the step d-5), in the lead memory module LM_Block, the LSTM layer has a hidden_size=256, and the one-dimensional convolutional layer includes a convolutional kernel with a size of 3; and in the step d-6), in the third branch, the first one-dimensional convolutional layer includes a convolutional kernel with a size of 32, the second one-dimensional convolutional layer includes a convolutional kernel with a size of 16, and the third one-dimensional convolutional layer includes a convolutional kernel with a size of 3.

Further, the step e) includes:

e-1) constructing the feature dimensionality reconstruction module, including a convolutional layer, a linear layer, and a Relu activation function in sequence; and e-2) inputting the encoded sequence X into the feature dimensionality reconstruction module, and outputting the dimensionality-reconstructed lead feature $X_g$; and inputting the encoded sequence Y into the feature dimensionality reconstruction module, and outputting the dimensionality-reconstructed lead feature $Y_g$.

Further, the step h) includes:

h-1) inputting the preprocessed ECG signal Z' into the one-dimensional convolutional layer of the trained encoder module, and outputting a feature $Z_{c1}$;

h-2) inputting the feature $Z_{c1}$ into the first convolutional block in the first branch of the time-domain fusion module TCFN of the trained encoder module, and outputting a feature $Z_{c1}^1$; inputting the feature $Z_{c1}^1$ into the second convolutional block in the first branch of the time-domain fusion module TCFN of the trained encoder module, and outputting a feature $Z_{c1}^2$; inputting the feature $Z_{c1}^2$ into the third convolutional block in the first branch of the time-domain fusion module TCFN of the trained encoder module, and outputting a feature $Z_{c1}^3$; and inputting the feature $Z_{c1}^3$ into the fourth convolutional block in the first branch of the time-domain fusion module TCFN of the trained encoder module, and outputting a feature $Z_{c1}'$;

h-3) inputting the feature $Z_{c1}$ into the lead memory module LM_Block in the second branch of the time-domain fusion module TCFN of the trained encoder module, and outputting a feature $Z_{c11}$; and inputting the feature $Z_{c11}$ and the feature $Z_{c1}$ into the skip connection module in the second branch of the time-domain fusion module TCFN of the trained encoder module for an addition operation to acquire a feature $Z_{c1}''$;

h-4) inputting the feature $Z_{c1}$ into the attention module in the third branch of the time-domain fusion module TCFN of the trained encoder module, and performing, by the torch.nn.MultiheadAttention function in python, an attention operation on the feature $Z_{c1}$ to obtain a resulting feature; and inputting the resulting feature into the first one-dimensional convolutional layer, the second one-dimensional convolutional layer, the third one-dimensional convolutional layer, and the maximum pooling layer in the third branch of the time-domain fusion module TCFN of the trained encoder module in sequence, and outputting an encoded sequence $Z_{c1}'''$; and h-5) subjecting the feature $Z_{c1}'$, the feature $Z_{c1}''$, and the encoded sequence $Z_{c1}'''$ to addition and averaging to acquire a feature $Z_{c2}$; and inputting the feature $Z_{c2}$ into the average pooling layer and the Dropout layer of the trained encoder module in sequence, and outputting the encoded sequence $Z_c$.

Further, the step j) includes:

j-1) inputting the lead feature $Z_g$ into a fully connected layer and a softmax activation function in sequence, and outputting a probability distribution from 0 to 1; and j-2) processing, by an argmax function in a python library numpy, the probability distribution, and outputting the final class.

The present disclosure has the following beneficial effects:

(1) The present disclosure applies self-supervised learning for ECG classification and prediction, reducing the problem of poor generalization ability of the model caused by differences in data sets, and improving the versatility of the ECG classification model.

(2) The present disclosure designs a residual-like structure with an attention module for extracting information from multiple leads in an ECG signal through self-supervised learning. The attention mechanism enables the encoder module to focus on important signal parts to adaptively adjust weight parameters and weight information from different leads, improving the efficiency and ability of the encoder module in feature extraction of the ECG signal.

(3) The present disclosure combines the feature of the ECG signal to perform targeted processing on the data augmentation part, and adopts Gaussian noise and space-time flipping. Due to factors such as electrode position and muscle activity interference, there is often some noise in the acquired ECG signal. Therefore, when performing data augmentation, selectively adding a certain amount of Gaussian noise interference to the overall signal can offset the impact of local noise on the overall feature of the signal. The ECG signal has a certain degree of space-time invariance. Based on the feature of the ECG signal, the data augmentation adopts space-time flipping to highlight the feature of the ECG signal, which facilitates extraction.

(4) The self-supervised learning network of the present disclosure combines a LSTM network and a multilayer perceptron to achieve prediction encoding and classification. Compared to ordinary convolution methods, the present disclosure can extract more temporal information from the ECG signal, improving classification accuracy.

DETAILED DESCRIPTION OF THE EMBODIMENTS

Figure 1:
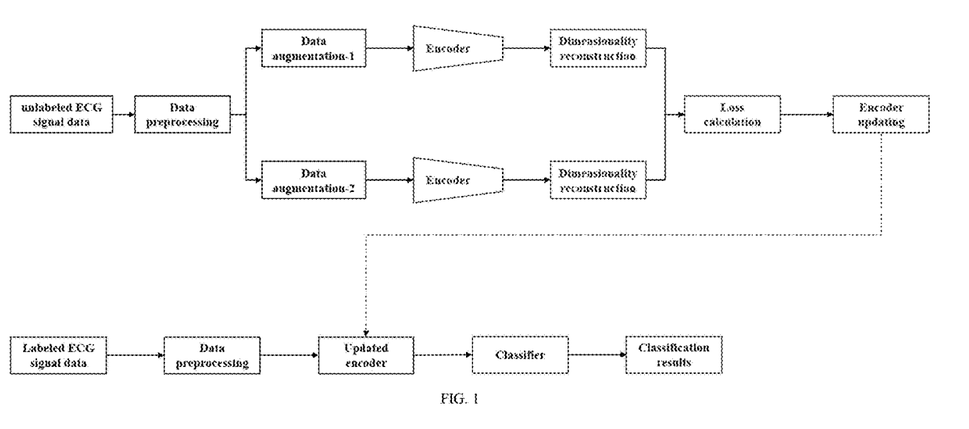
FIG. 1 is a flowchart of a method according to the present disclosure.

The present disclosure will be described in detail below with reference to FIG. 1.

A multi-lead ECG signal classification method based on self-supervised learning includes the following steps:

a) Original ECG signal data X is acquired.

b) The original ECG signal data X is preprocessed to acquire preprocessed ECG signal X'.

c) A data augmentation unit is constructed, the preprocessed ECG signal X' is input into the data augmentation module, and augmented positive sample $X_a$ and augmented negative sample $Y_a$ are output.

d) An encoder module is constructed. The augmented positive sample $X_a$ is input into the encoder module, and encoded sequence $X_c$ is output. The augmented negative sample $Y_a$ is input into the encoder module, and encoded sequence $Y_c$ is output.

e) A feature dimensionality reconstruction module is constructed. The encoded sequence $X_c$ is input into the feature dimensionality reconstruction module, and dimensionality-reconstructed lead feature $X_g$ is output. The encoded sequence $Y_c$ is input into the feature dimensionality reconstruction module, and dimensionality-reconstructed lead feature $Y_g$ is output.

f) The encoder module is trained by an adaptive moment estimation (Adam) optimizer through a contrastive learning loss to acquire a trained encoder module.

g) The original ECG signal data X in the step b) is replaced with ECG signal data Z that needs classification, and the step b) is repeated to acquire preprocessed ECG signal Z'.

h) The preprocessed ECG signal Z' is input into the trained encoder module, and encoded sequence $Z_c$ is output.

i) The encoded sequence $X_c$ in the step e) is replaced with the encoded sequence $Z_c$, and the step e) is repeated to acquire dimensionality-reconstructed lead feature $Z_g$.

j) A final class is acquired based on the lead feature $Z_g$.

The present disclosure relates to upstream and downstream tasks. The upstream task is to train the encoder module. Firstly, based on the original ECG sample, a positive-negative sample pair is generated through different data augmentation methods. Corresponding encoded results are acquired by encoding the sample through the encoder module. A loss function is used to compare differences between the encoded results and calculate a loss. The parameters of the encoder are updated through backpropagation, thus achieving the goal of finding an optimal encoder. The downstream task is to predict a training result and apply the trained encoder module to classify the ECG signal.

In an embodiment of the present disclosure, in the step a), an ECG signal is acquired from a PhysioNet2020 dataset. The acquired ECG signal is resampled by a resample( ) function in a Python library sklearn.utils. a length of the ECG signal is adjusted to L sample points to acquire the original ECG signal data X, $X \in R^{C \times L}$, where R denotes a real number space, and C denotes a number of channels, which is equal to a number of leads of the ECG signal, so C=12. In the embodiment, preferably, L=1000.

In an embodiment of the present disclosure, the step b) is as follows.

b-1) A signal.butter method is called by python from a scipy module, and denoising and baseline wander removal are performed on the original ECG signal data X by a Butterworth bandpass filter with a cutoff frequency including a low frequency of 0.5 Hz and a high frequency of 49 Hz.

b-2) The resample( ) function in the Python library sklearn.utils resamples an acquired ECG signal for each lead in the original ECG signal data X after denoising and baseline wander removal. A length of the ECG signal is adjusted to L to acquire the preprocessed ECG signal X'.

In an embodiment of the present disclosure, the step c) is as follows.

c-1) The data augmentation unit is constructed, including a first augmentation module and a second augmentation module.

c-2) The preprocessed ECG signal X' is input into the first augmentation module, and a value of each lead signal in the preprocessed ECG signal X' is multiplied by −1 to acquire the augmented positive sample $X_a$.

c-3) The preprocessed ECG signal X' is input into the second augmentation module, and data augmentation is performed on the preprocessed ECG signal X' through Gaussian noise (GN) to acquire the augmented negative sample $Y_a$.

In an embodiment of the present disclosure, the step d) is as follows.

d-1) The encoder module is constructed, including a one-dimensional convolutional layer, a time-domain fusion module temporal convolutional fusion network (TCFN), an average pooling layer, and a Dropout layer.

d-2) The augmented positive sample $X_a$ is input into the one-dimensional convolutional layer, and feature $X_{c1}$ is output. The augmented negative sample $Y_a$ is input into the one-dimensional convolutional layer, and feature $Y_{c1}$ is output.

d-3) The time-domain fusion module TCFN is divided into a first branch, a second branch, and a third branch.

d-4) The first branch is constructed, including a first convolutional block, a second convolutional block, a third convolutional block, and a fourth convolutional block, where each of the first convolutional block, the second convolutional block, the third convolutional block, and the fourth convolutional block includes a first convolutional layer, a second convolutional layer, a BatchNormal1d layer, a rectified linear unit (ReLU) layer, a MaxPool1d layer, and a Dropout layer in sequence. The feature $X_{c1}$ is input into the first convolutional block in the first branch, and feature $X_{c1}^1$ is output. The feature $X_{c1}^1$ is input into the second convolutional block in the first branch, and feature $X_{c1}^2$ is output. The feature $X_{c1}^2$ is input into the third convolutional block in the first branch, and feature $X_{c1}^3$ is output. The feature $X_{c1}^3$ is input into the fourth convolutional block in the first branch, and feature $X_{c1}'$ is output. The feature $Y_{c1}$ is input into the first convolutional block in the first branch, and feature $Y_{c1}^1$ is output. The feature $Y_{c1}^1$ is input into the second convolutional block in the first branch, and feature $Y_{c1}^2$ is output. The feature $Y_{c1}^2$ is input into the third convolutional block in the first branch, and feature $Y_{c1}^3$ is output. The feature $Y_{c1}^3$ is input into the fourth convolutional block in the first branch, and feature $Y_{c1}'$ is output.

d-5) The second branch is constructed, including a lead memory module LM_Block and a skip connection module, where the lead memory module LM_Block includes a global pooling layer, a long short-term memory (LSTM) layer, a one-dimensional convolutional layer, and a Relu activation function in sequence. The feature $X_{c1}$ is input into the lead memory module LM_Block, and feature $X_{c11}$ is output. The feature $X_{c11}$ and the feature $X_{c1}$ are input into the skip connection module for an addition operation to acquire feature $X_{c1}''$. The feature $Y_{c1}$ is input into the lead memory module LM_Block, and feature $Y_{c11}$ is output. The feature $Y_{c11}$ and the feature $Y_{c1}$ are input into the skip connection module for an addition operation to acquire feature $Y_{c1}''$.

d-6) The third branch is constructed, including an attention module, a first one-dimensional convolutional layer, a second one-dimensional convolutional layer, a third one-dimensional convolutional layer, and a maximum pooling layer, for improving global perception ability. The feature $X_{c1}$ is input into the attention module, and an attention operation is performed on the feature $X_{c1}$ by a torch.nn.MultiheadAttention function in python to obtain a resulting feature. The resulting feature is input into the first one-dimensional convolutional layer, the second one-dimensional convolutional layer, the third one-dimensional convolutional layer, and the maximum pooling layer in sequence, and encoded sequence $X_{c1}'''$ is output. The feature $Y_{c1}$ is input into the attention module, and an attention operation is performed on the feature $Y_{c1}$ by the torch.nn.MultiheadAttention function in python to obtain a resulting feature. The resulting feature is input into the first one-dimensional convolutional layer, the second one-dimensional convolutional layer, the third one-dimensional convolutional layer, and the maximum pooling layer in sequence, and encoded sequence $Y_{c1}'''$ is output.

d-7) The feature $X_{c1}'$, the feature $X_{c1}''$, and the encoded sequence $X_{c1}'''$ are subjected to addition and averaging to acquire a feature $X_{c2}$. The feature $Y_{c1}'$, the feature $Y_{c1}''$, and the encoded sequence $Y_{c1}'''$ are subjected to addition and averaging to acquire a feature $Y_{c2}$. The feature $X_{c2}$ is input into the average pooling layer and the Dropout layer of the encoder module in sequence, and the encoded sequence $X_c$ is output. The feature $Y_{c2}$ is input into the average pooling layer and the Dropout layer of the encoder module in sequence, and the encoded sequence $Y_c$ is output.

In this embodiment, preferably, in the step d-1), the one-dimensional convolutional layer of the encoder module includes a convolutional kernel with a size of 3. In the step d-4), each of the first convolutional layer and the second convolutional layer in the first convolutional block includes a convolutional kernel with a size of 64, each of the first convolutional layer and the second convolutional layer in the second convolutional block includes a convolutional kernel with a size of 32, each of the first convolutional layer and the second convolutional layer in the third convolutional block includes a convolutional kernel with a size of 16, and each of the first convolutional layer and the second convolutional layer in the fourth convolutional block includes a convolutional kernel with a size of 3. In the step d-5), in the lead memory module LM_Block, the LSTM layer has a hidden_size=256, and the one-dimensional convolutional layer includes a convolutional kernel with a size of 3. In the step d-6), in the third branch, the first one-dimensional convolutional layer includes a convolutional kernel with a size of 32, the second one-dimensional convolutional layer includes a convolutional kernel with a size of 16, and the third one-dimensional convolutional layer includes a convolutional kernel with a size of 3.

In an embodiment of the present disclosure, the step e) is as follows.
- e-1) The feature dimensionality reconstruction module is constructed, including a convolutional layer, a linear layer, and a Relu activation function in sequence.
- e-2) The encoded sequence $X_c$ is input into the feature dimensionality is reconstruction module, and the dimensionality-reconstructed lead feature $X_g$ output. The encoded sequence $Y_c$ is input into the feature dimensionality reconstruction module, and the dimensionality-reconstructed lead feature $Y_g$ is output.

In an embodiment of the present disclosure, the step h) is as follows.
- h-1) The preprocessed ECG signal Z' is input into the one-dimensional convolutional layer of the trained encoder module, and feature $Z_{c1}$ is output.
- h-2) The feature $Z_{c1}$ is input into the first convolutional block in the first branch of the time-domain fusion module TCFN of the trained encoder module, and feature $Z_{c1}^1$ is output. The feature $Z_{c1}^1$ is input into the second convolutional block in the first branch of the time-domain fusion module TCFN of the trained encoder module, and feature $Z_{c1}^2$ is output. The feature $Z_{c1}^2$ is input into the third convolutional block in the first branch of the time-domain fusion module TCFN of the trained encoder module, and feature $Z_{c1}^3$ is output. The feature $Z_{c1}^3$ is input into the fourth convolutional block in the first branch of the time-domain fusion module TCFN of the trained encoder module, and feature $Z_{c1}'$ is output.
- h-3) The feature $Z_{c1}$ is input into the lead memory module LM_Block in the second branch of the time-domain fusion module TCFN of the trained encoder module, and feature $Z_{c11}$ is output. The feature $Z_{c11}$ and the feature $Z_{c1}$ are input into the skip connection module in the second branch of the time-domain fusion module TCFN of the trained encoder module for an addition operation to acquire feature $Z_{c1}''$.
- h-4) The feature $Z_{c1}$ is input into the attention module in the third branch of the time-domain fusion module TCFN of the trained encoder module, and an attention operation is performed on the feature $Z_{c1}$ by the torch.nn.MultiheadAttention function in python to obtain a resulting feature. The resulting feature is input into the first one-dimensional convolutional layer, the second one-dimensional convolutional layer, the third one-dimensional convolutional layer, and the maximum pooling layer in the third branch of the time-domain fusion module TCFN of the trained encoder module in sequence, and encoded sequence $Z_{c1}'''$ is output.
- h-5) The feature $Z_{c1}'$, the feature $Z_{c1}''$, and the encoded sequence $Z_{c1}'''$ are subjected to addition and averaging to acquire a feature $Z_{c2}$. The feature $Z_{c2}$ is input into the average pooling layer and the Dropout layer of the trained encoder module in sequence, and the encoded sequence $Z_c$ is output.

In an embodiment of the present disclosure, the step j) is as follows.
- j-1) The lead feature $Z_g$ is input into a fully connected layer and a softmax activation function in sequence, and a probability distribution from 0 to 1 is output.
- j-2) The probability distribution is processed by an argmax function in a python library numpy, and the final class is output.

Figure 2:
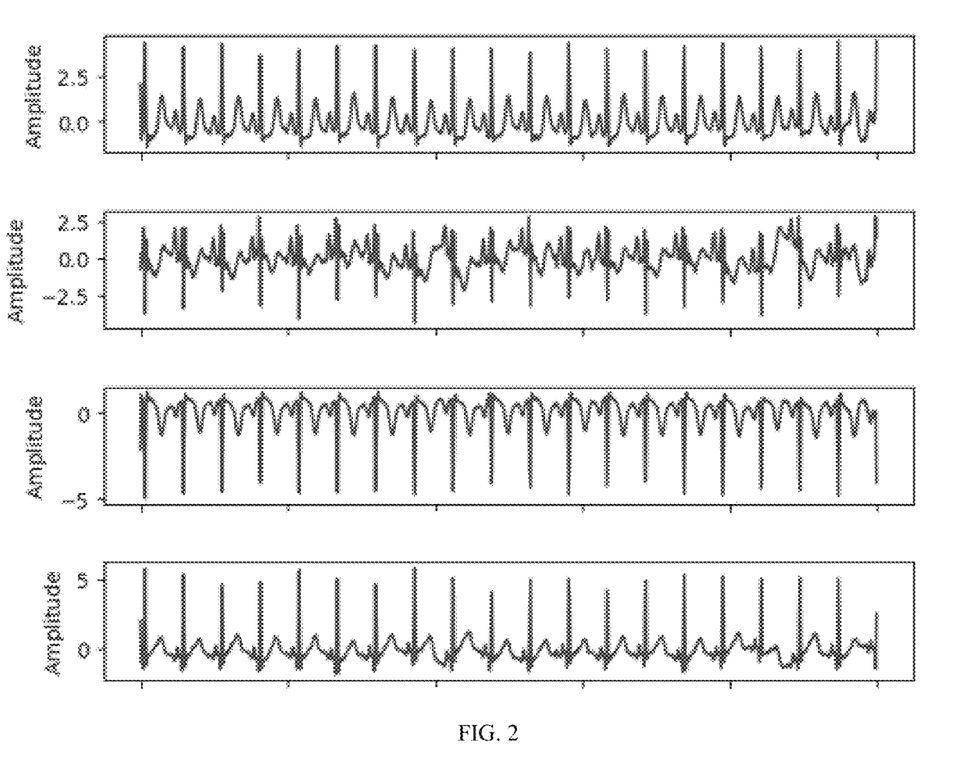
FIG. 2 shows an original ECG signal.
Figure 3:
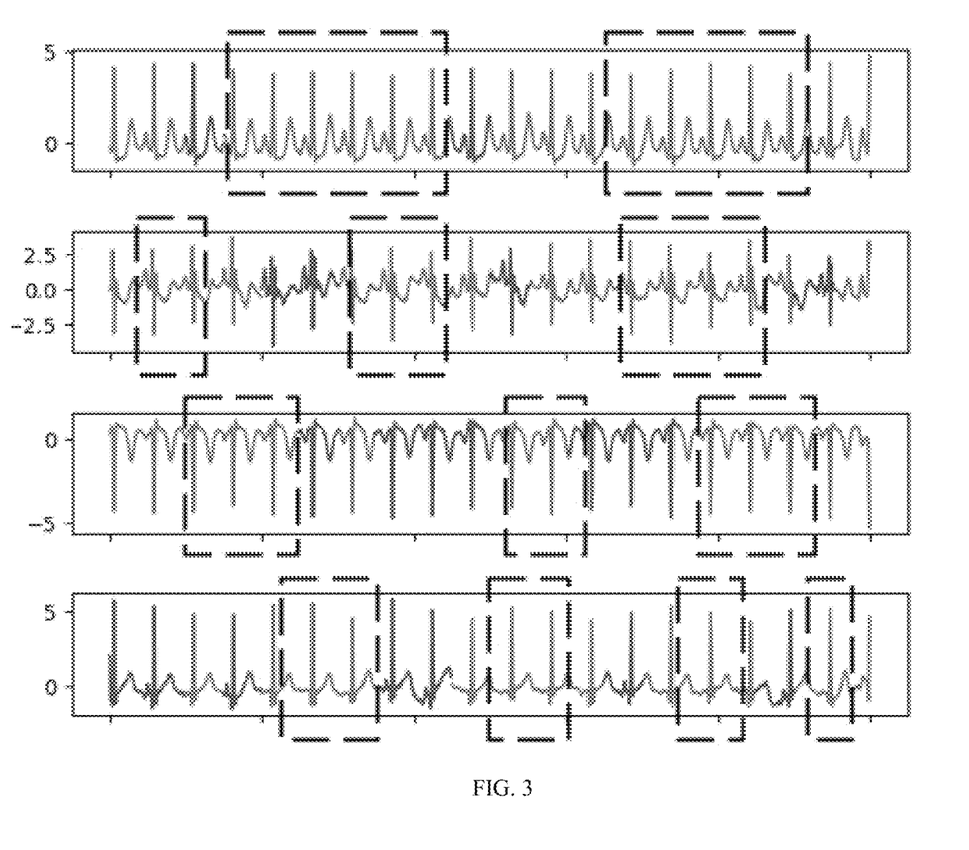
FIG. 3 shows an augmented ECG signal.
Figure 4A:
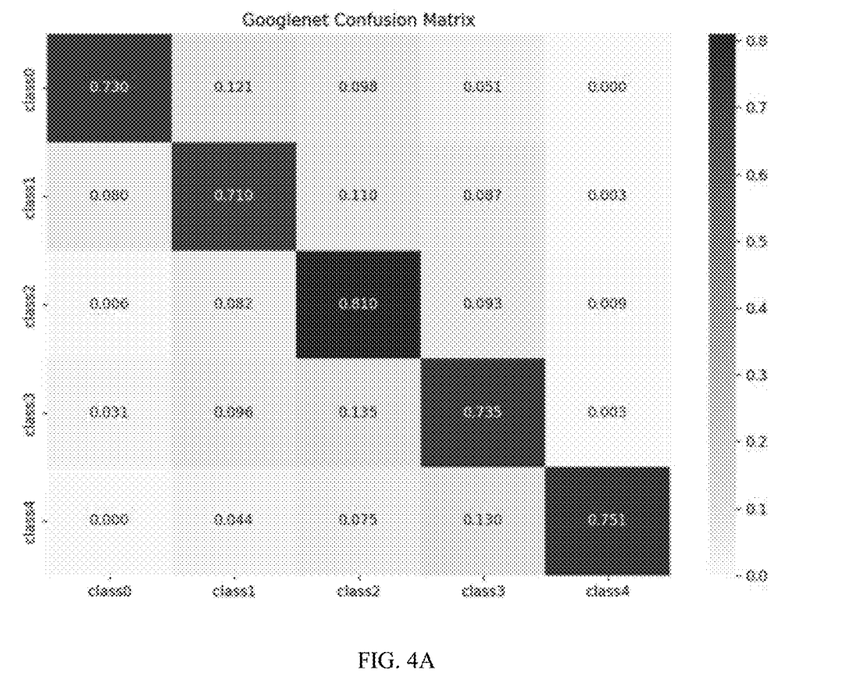
FIGS. 4A-4E show comparison of confusion matrices for different models.
Figure 4B:
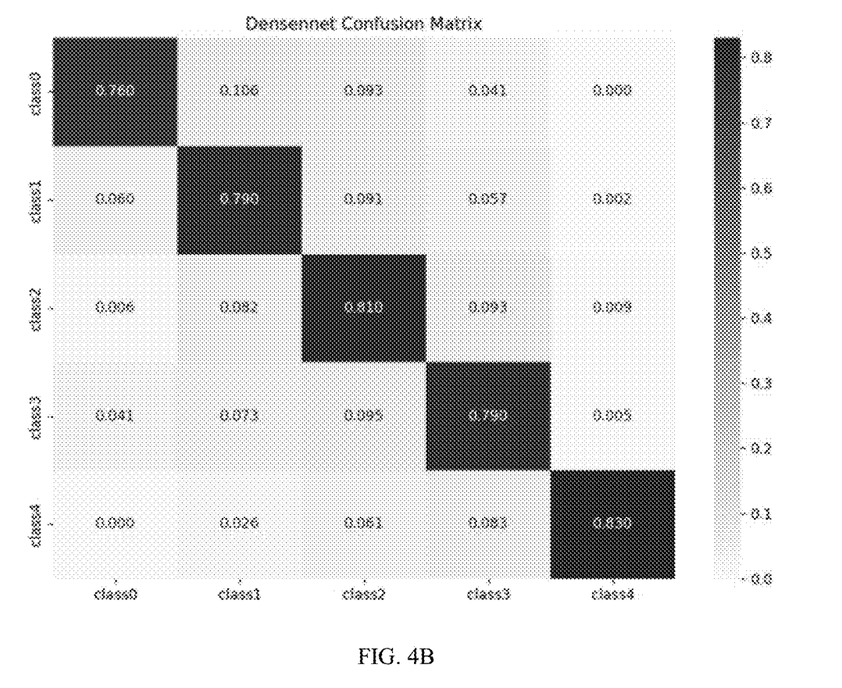
Figure 4C:
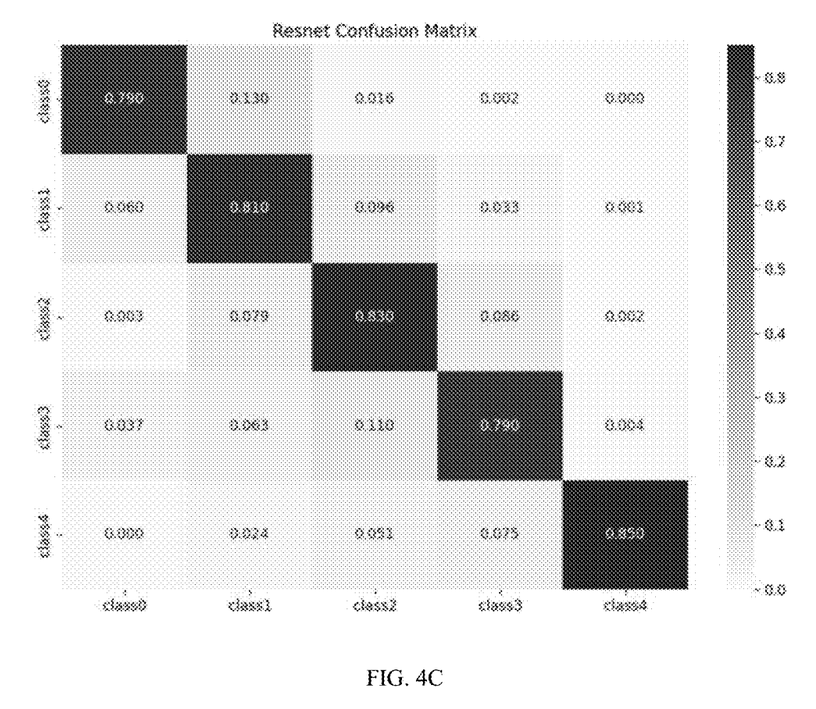
Figure 4D:
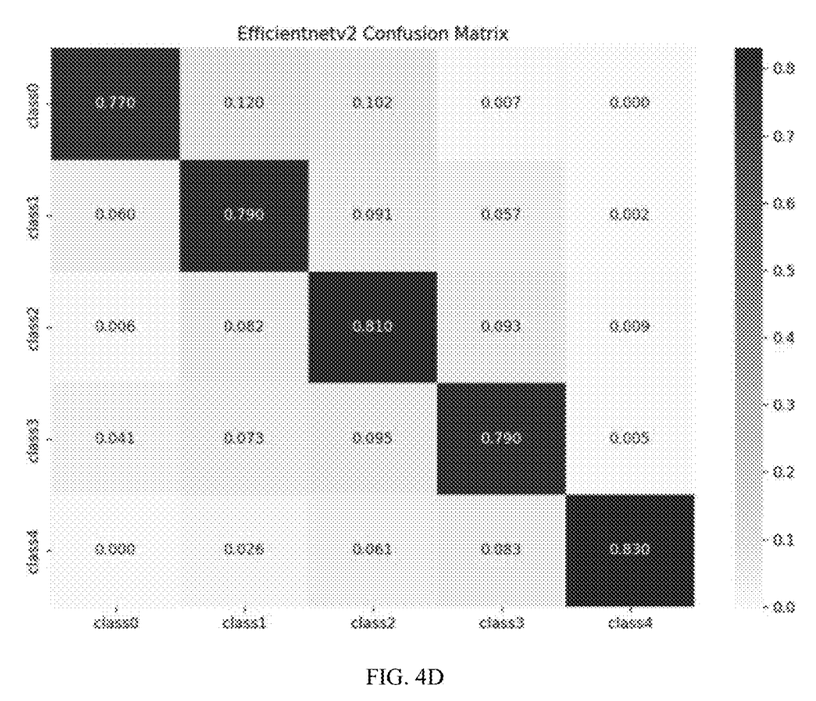
Figure 4E:
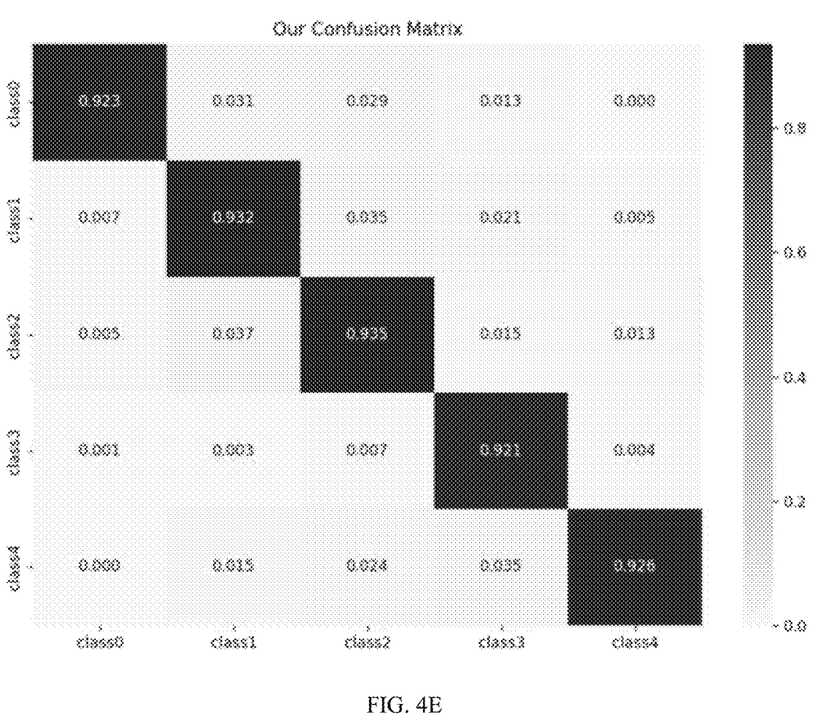

FIG. 2 shows three randomly selected signals, and FIG. 3 shows new signals acquired by data augmentation on four randomly selected ECG signal segments. The signal segments outlined in dashed circles are clearly different from the original signal, which indicates the necessity of data augmentation that can learn more feature information of the ECG signal from these differences through self-supervised learning.

The model proposed by the present disclosure, mainstream classification task models (Googlenet, ResnetNet50, Densennet), and a lightweight model (Efficientnet) each are combined with a self-supervised learning method, i.e. SimCLR method, and the combination results are compared. All comparative models are validated under uniform experimental conditions, and the hyperparameters of all network architectures are manually adjusted to the optimal level. Accuracy, sensitivity, precision, and F1 score are used as evaluation metrics.

TABLE 1

| Method | Lineaer Evaluation | Transfer Learning |
| --- | --- | --- |
| SimCLR + Googlenet | 0.789 | 0.817 |
| SimCLR + ResNet50 | 0.776 | 0.851 |
| SimCLR + Efficientnet | 0.791 | 0.863 |
| SimCLR + Densennet | 0.813 | 0.866 |
| SimCLR + OursModel | 0.853 | 0.891 |

Table 1 gives area under the receiver operating characteristic (AUROC) results of different models on PhysioNet 2020 dataset. Table 1 shows the different AUROC values acquired by linear fine-tuning and transfer learning on the PhysioNet 2020 dataset using different methods. From Table 1, it can be seen that the downstream fine-tuning task has a certain effect on improving classification performance, and the proposed model has certain advantages over other models when using the same method.

TABLE 2

| Method | Accuracy (%) | Sensitivity (%) | Precision (%) | F1 Score (%) |
| --- | --- | --- | --- | --- |
| SimCLR + Googlenet | 83.16 | 83.37 | 83.33 | 83.14 |
| SimCLR + ResNet50 | 85.16 | 85.37 | 85.31 | 86.02 |
| SimCLR + Efficientnet | 83.03 | 83.17 | 82.96 | 83.06 |
| SimCLR + Densennet | 88.16 | 88.25 | 88.15 | 87.98 |
| SimCLR + OurModel | 90.16 | 90.05 | 90.19 | 90.14 |

Table 2 shows comparison results of different model methods on PhysioNet 2020 dataset. Based on other evaluation metrics and statistical data in Table 2, the proposed model exhibits superior classification performance compared to the mainstream classification models such as Densennet and Resnet. The proposed model exhibits higher levels of accuracy, precision, recall, and F1 score. This indicates that the proposed model has superior overall performance, and can reduce the risk of misdiagnosis during evaluation, and provide more reliable signals for subsequent tasks. FIGS. 4A-4E show the training results of different models using a confusion matrix. In self-supervised learning, the proposed model outperforms other models on classification tasks. In summary, from the perspective of model performance, the proposed model has excellent ability to distinguish ECG signals in practical environments and shows strong capabilities in practical application environments.

Finally, it should be noted that the above descriptions are only preferred embodiments of the present disclosure, and are not intended to limit the present disclosure. Although the present disclosure has been described in detail with reference to the foregoing embodiments, those skilled in the art may still modify the technical solutions described in the foregoing embodiments, or equivalently substitute some technical features thereof. Any modification, equivalent substitution, improvement, etc. within the spirit and principles of the present disclosure shall fall within the scope of protection of the present disclosure.

What is claimed is:

1. A multi-lead electrocardiogram (ECG) signal classification method based on self-supervised learning, comprising the following steps:
   a) acquiring original ECG signal data X;
   b) preprocessing the original ECG signal data X to acquire a preprocessed ECG signal X';
   c) constructing a data augmentation unit, inputting the preprocessed ECG signal X' into the data augmentation unit, and outputting an augmented positive sample $X_a$ and an augmented negative sample $Y_a$;
   d) constructing an encoder module; inputting the augmented positive sample $X_a$ into the encoder module, and outputting an encoded sequence $X_c$; and inputting the augmented negative sample $Y_a$ into the encoder module, and outputting an encoded sequence $Y_c$;
   e) constructing a feature dimensionality reconstruction module; inputting the encoded sequence $X_c$ into the feature dimensionality reconstruction module, and outputting a dimensionality-reconstructed lead feature $X_g$; and inputting the encoded sequence $Y_c$ into the feature dimensionality reconstruction module, and outputting a dimensionality-reconstructed lead feature $Y_g$;
   f) training, by an adaptive moment estimation (Adam) optimizer, the encoder module through a contrastive learning loss to acquire a trained encoder module;
   g) replacing the original ECG signal data X in the step b) with ECG signal data Z that needs classification, and repeating the step b) to acquire a preprocessed ECG signal Z';
   h) inputting the preprocessed ECG signal Z' into the trained encoder module, and outputting an encoded sequence $Z_c$;
   i) replacing the encoded sequence $X_c$ in the step e) with the encoded sequence $Z_c$, and repeating the step e) to acquire a dimensionality-reconstructed lead feature $Z_g$; and
   j) acquiring a final class based on the dimensionality-reconstructed lead feature $Z_g$;
   wherein the step d) comprises:
      d-1) constructing the encoder module, comprising a one-dimensional convolutional layer, a time-domain fusion module temporal convolutional fusion network (TCFN), an average pooling layer, and a Dropout layer;
      d-2) inputting the augmented positive sample $X_a$ into the one-dimensional convolutional layer, and outputting a feature $X_{c1}$; and inputting the augmented negative sample $Y_a$ into the one-dimensional convolutional layer, and outputting a feature $Y_{c1}$;
      d-3) dividing the TCFN into a first branch, a second branch, and a third branch;
      d-4) constructing the first branch, comprising a first convolutional block, a second convolutional block, a third convolutional block, and a fourth convolutional block, wherein each of the first convolutional block, the second convolutional block, the third convolutional block, and the fourth convolutional block comprises a first convolutional layer, a second convolutional layer, a BatchNormal1d layer, a rectified linear unit (ReLU) layer, a MaxPool1d layer, and a Dropout layer in sequence; inputting the feature $X_{c1}$ into the first convolutional block in the first branch, and outputting a feature $X_{c1}^1$; inputting the feature $X_{c1}^1$ into the second convolutional block in the first branch, and outputting a feature $X_{c1}^2$; inputting the feature $X_{c1}^2$ into the third convolutional block in the first branch, and outputting a feature outputting a feature $X_{c1}^3$; inputting the feature $X_{c1}^3$ into the fourth convolutional block in the first branch, and outputting a feature $X_{c1}'$; inputting the feature $Y_{c1}$ into the first convolutional block in the first branch, and outputting a feature $Y_{c1}^1$; inputting the feature $Y_{c1}^1$ into the second convolutional block in the first branch, and outputting a feature $Y_{c1}^2$; inputting the feature $Y_{c1}^2$ into the third convolutional block in the first branch, and outputting a feature $Y_{c1}^3$; and inputting the feature $Y_{c1}^3$ into the fourth convolutional block in the first branch, and outputting a feature $Y_{c1}'$,
      d-5) constructing the second branch, comprising a lead memory block (LM_Block) and a skip connection module, wherein the LM_Block comprises a global pooling layer, a long short-term memory (LSTM) layer, a one-dimensional convolutional layer, and a ReLU activation function in sequence; inputting the feature $X_{c1}$ into the LM_Block, and outputting a feature $X_{c1}^1$; inputting the feature $X_{c11}$ and the feature $X_{c1}$ into the skip connection module for a first addition operation to acquire a feature $X_{c1}''$; inputting the feature $Y_{c1}$ into the LM_Block, and outputting a feature $Y_{c11}$; and inputting the feature $Y_{c11}$ and the feature $Y_{c1}$ into the skip connection module for a second addition operation to acquire a feature $Y_{c1}''$;
      d-6) constructing the third branch, comprising an attention module, a first one-dimensional convolutional layer, a second one-dimensional convolutional layer, a third one-dimensional convolutional layer, and a maximum pooling layer; inputting the feature $X_{c1}$ into the attention module, and performing, by a torch.nn.MultiheadAttention function in Python programming language, a first attention operation on the feature $X_{c1}$ to obtain a first resulting feature; inputting the first resulting feature into the first one-dimensional convolutional layer, the second one-dimensional convolutional layer, the third one-dimensional convolutional layer, and the maximum pooling layer in sequence, and outputting an encoded sequence $X_{c1}'''$; inputting the feature $Y_{c1}$ into the attention module, and performing, by the torch.nn.MultiheadAttention function in Python programming language, a second attention operation on the feature $Y_{c1}$ to obtain a second resulting feature; and inputting the second resulting feature into the first one-dimensional convolutional layer, the second one-dimensional convolutional layer, the third one-dimensional convolutional layer, and the maximum pooling layer in sequence, and outputting an encoded sequence $Y_{c1}'''$; and d-7) subjecting the feature $X_{c1}'$, the feature $X_{c1}''$, and the encoded sequence $X_{c1}'''$ to addition and averaging to acquire a feature $X_{c2}$; subjecting the feature $Y_{c1}'$, the feature $Y_{c1}''$, and the encoded sequence $Y_{c1}'''$ to addition and averaging to acquire a feature $Y_{c2}$; inputting the feature $X_{c2}$ into the average pooling layer and the Dropout layer of the encoder module in sequence, and outputting the encoded sequence $X_c$; and inputting the feature $Y_{c2}$ into the average pooling layer and the Dropout layer of the encoder module in sequence, and outputting the encoded sequence $Y_c$.

2. The multi-lead ECG signal classification method based on self-supervised learning according to claim 1, wherein the step a) comprises: acquiring an ECG signal from a PhysioNet2020 dataset, resampling the ECG signal by a resample function in a sklearn.utils Python programming language library, and adjusting a length of the ECG signal to L sample points to acquire the original ECG signal data X, $X \in R^{C \times L}$, wherein R denotes a real number space, and C denotes a number of channels.

3. The multi-lead ECG signal classification method based on self-supervised learning according to claim 2, wherein C=12, and L=1000.

4. The multi-lead ECG signal classification method based on self-supervised learning according to claim 1, wherein the step b) comprises:
   b-1) calling a signal.butter method from a SciPy Python programming language library; and performing, by a Butterworth bandpass filter with a cutoff frequency comprising a low frequency of 0.5 Hz and a high frequency of 49 Hz, denoising and baseline wander removal on the original ECG signal data X; and
   b-2) resampling, by a resample function in a sklearn.utils Python programming language library, an acquired ECG signal for each lead in the original ECG signal data X after denoising and baseline wander removal; and adjusting a length of the acquired ECG signal to L to acquire the preprocessed ECG signal X'.

5. The multi-lead ECG signal classification method based on self-supervised learning according to claim 1, wherein the step c) comprises:
   c-1) constructing the data augmentation unit, comprising a first augmentation module and a second augmentation module;
   c-2) inputting the preprocessed ECG signal X' into the first augmentation module, and multiplying a value of each lead signal in the preprocessed ECG signal X' by −1 to acquire the augmented positive sample $X_a$; and
   c-3) inputting the preprocessed ECG signal X' into the second augmentation module, and performing data augmentation on the preprocessed ECG signal X' through Gaussian noise to acquire the augmented negative sample $Y_a$.

6. The multi-lead ECG signal classification method based on self-supervised learning according to claim 1, wherein in the step d-1), the one-dimensional convolutional layer of the encoder module comprises a convolutional kernel with a size of 3; in the step d-4), each of the first convolutional layer and the second convolutional layer in the first convolutional block comprises a convolutional kernel with a size of 64, each of the first convolutional layer and the second convolutional layer in the second convolutional block comprises a convolutional kernel with a size of 32, each of the first convolutional layer and the second convolutional layer in the third convolutional block comprises a convolutional kernel with a size of 16, and each of the first convolutional layer and the second convolutional layer in the fourth convolutional block comprises a convolutional kernel with a size of 3; in the step d-5), in the LM_Block, the LSTM layer has a hidden_size=256, and the one-dimensional convolutional layer comprises a convolutional kernel with a size of 3; and in the step d-6), in the third branch, the first one-dimensional convolutional layer comprises a convolutional kernel with a size of 32, the second one-dimensional convolutional layer comprises a convolutional kernel with a size of 16, and the third one-dimensional convolutional layer comprises a convolutional kernel with a size of 3.

7. The multi-lead ECG signal classification method based on self-supervised learning according to claim 1, wherein the step e) comprises:
   e-1) constructing the feature dimensionality reconstruction module, comprising a convolutional layer, a linear layer, and a ReLU activation function in sequence; and
   e-2) inputting the encoded sequence $X_c$ into the feature dimensionality reconstruction module, and outputting the dimensionality-reconstructed lead feature $X_g$; and inputting the encoded sequence $Y_c$ into the feature dimensionality reconstruction module, and outputting the dimensionality-reconstructed lead feature $Y_g$.

8. The multi-lead ECG signal classification method based on self-supervised learning according to claim 1, wherein the step h) comprises:
   h-1) inputting the preprocessed ECG signal Z' into the one-dimensional convolutional layer of the trained encoder module, and outputting a feature $Z_{c1}$;
   h-2) inputting the feature $Z_{c1}$ into the first convolutional block in the first branch of the TCFN of the trained encoder module, and outputting a feature $Z_{c1}^1$; inputting the feature $Z_{c1}^1$ into the second convolutional block in the first branch of the TCFN of the trained encoder module, and outputting a feature $Z_{c1}^2$; inputting the feature $Z_{c1}^2$ into the third convolutional block in the first branch of the TCFN of the trained encoder module, and outputting a feature $Z_{c1}^3$; and inputting the feature $Z_{c1}^3$ into the fourth convolutional block in the first branch of the TCFN of the trained encoder module, and outputting a feature $Z_{c1}'$;
   h-3) inputting the feature $Z_{c1}$ into the lead memory module LM_Block in the second branch of the TCFN of the trained encoder module, and outputting a feature $Z_{c11}$; and inputting the feature $Z_{c11}$ and the feature $Z_{c1}$ into the skip connection module in the second branch of the TCFN of the trained encoder module for a third addition operation to acquire a feature $Z_{c1}''$;
   h-4) inputting the feature $Z_{c1}$ into the attention module in the third branch of the time-domain fusion module TCFN of the trained encoder module, and performing, by the torch.nn.MultiheadAttention function in Python programming language, a third attention operation on the feature $Z_{c1}$ to obtain a third resulting feature; and inputting the third resulting feature into the first one-dimensional convolutional layer, the second one-dimensional convolutional layer, the third one-dimensional convolutional layer, and the maximum pooling layer in the third branch of the TCFN of the trained encoder module in sequence, and outputting an encoded sequence $Z_{c1}'''$; and
   h-5) subjecting the feature $Z_{c1}'$, the feature $Z_{c1}''$, and the encoded sequence $Z_{c1}'''$ to addition and averaging to acquire a feature $Z_{c2}$; and inputting the feature $Z_{c2}$, into the average pooling layer and the Dropout layer of the trained encoder module in sequence, and outputting the encoded sequence $Z_c$.

9. The multi-lead ECG signal classification method based on self-supervised learning according to claim 1, wherein the step j) comprises:
- j-1) inputting the dimensionality-reconstructed lead feature $Z_g$ into a fully connected layer and a softmax activation function in sequence, and outputting a probability distribution from 0 to 1; and
- j-2) processing, by an argmax function in a NumPy Python programming language library, the probability distribution, and outputting the final class.

* * * * *